(12) United States Patent
Chung et al.

(10) Patent No.: US 10,392,596 B2
(45) Date of Patent: Aug. 27, 2019

(54) HIGH THROUGHPUT PHOTOBIOREACTOR

(71) Applicants: KOREA RESEARCH INSTITUTE OF BIOSCIENCE AND BIOTECHNOLOGY, Daejeon (KR); Shin Hwa CHUNG, Daejeon (KR)

(72) Inventors: Shin Hwa Chung, Daejeon (KR); Hee Sik Kim, Daejeon (KR); Dae Hyun Cho, Daejeon (KR); Hee Mock Oh, Daejeon (KR); Jin A Heo, Daejeon (KR)

(73) Assignees: KOREA RESEARCH INSTITUTE OF BIOSCIENCE AND BIOTECHNOLOGY, Daejeon (KR); Shin Hwa Chung, Daejeon (KR)

( * ) Notice: Subject to any disclaimer, the term of this patent is extended or adjusted under 35 U.S.C. 154(b) by 0 days.

(21) Appl. No.: 15/694,140

(22) Filed: Sep. 1, 2017

(65) Prior Publication Data
US 2017/0362561 A1 Dec. 21, 2017

Related U.S. Application Data

(63) Continuation-in-part of application No. PCT/KR2016/002079, filed on Mar. 2, 2016.

(30) Foreign Application Priority Data

Mar. 3, 2015 (KR) .......................... 10-2015-0029732
Dec. 1, 2015 (KR) .......................... 10-2015-0170245

(51) Int. Cl.
*C12M 1/00* (2006.01)
*C12M 1/32* (2006.01)
(Continued)

(52) U.S. Cl.
CPC ............ *C12M 41/06* (2013.01); *C12M 21/02* (2013.01); *C12M 23/12* (2013.01); *C12M 27/16* (2013.01);
(Continued)

(58) Field of Classification Search
USPC ...................................... 435/286.1
See application file for complete search history.

(56) References Cited

U.S. PATENT DOCUMENTS 5,716,584 A * 2/1998 Baker .................. B01J 19/0046
422/297
2008/0032397 A1* 2/2008 Korpinen ............ B01L 3/50853
435/303.1
(Continued)

FOREIGN PATENT DOCUMENTS

KR 10-0283026 B1 3/2001
KR 10-2003-0018196 A 3/2003
(Continued)

OTHER PUBLICATIONS

Spilling et al., "Optimizing lipid production by planktonic algae-LIPIDO," May 2010, Nordic Energy Research, pp. 27-29 (Year: 2010).*
(Continued)

*Primary Examiner* — Kevin Joyner
*Assistant Examiner* — Holly M Mull
(74) *Attorney, Agent, or Firm* — Merchant & Gould P.C.

(57) ABSTRACT

Provided is a high throughput photobioreactor. The high throughput photobioreactor includes: a chamber; a plate installed in the chamber and mounted with a plurality of wells; a plurality of light sources installed in the chamber and irradiating light toward the plate; a light quantity controller positioned on an upper part of the plate to make quantities of light irradiated to the plurality of wells differ-
(Continued)

ent; and a temperature controller controlling a temperature of the plate.

19 Claims, 13 Drawing Sheets

(51) Int. Cl.
    *C12M 1/34*     (2006.01)
    *C12M 1/02*     (2006.01)
    *C12M 3/06*     (2006.01)

(52) U.S. Cl.
    CPC .............. *C12M 29/00* (2013.01); *C12M 29/06* (2013.01); *C12M 31/10* (2013.01); *C12M 41/12* (2013.01)

(56) References Cited

U.S. PATENT DOCUMENTS

| | | | | |
|---|---|---|---|---|
| 2011/0035160 | A1* | 2/2011 | Rhee | C12M 23/12 702/22 |
| 2013/0153938 | A1* | 6/2013 | Grajcar | F21V 3/061 257/88 |
| 2014/0331552 | A1* | 11/2014 | Lau | C12M 21/02 47/1.4 |
| 2015/0182969 | A1* | 7/2015 | Burroughs | B01L 3/50851 435/6.12 |
| 2015/0362476 | A1* | 12/2015 | Clements | G01N 21/01 506/10 |

FOREIGN PATENT DOCUMENTS

| | | |
|---|---|---|
| KR | 10-0842840 B1 | 7/2008 |
| KR | 10-2011-0000463 A | 1/2011 |
| KR | 10-2012-0124277 A | 11/2012 |
| KR | 10-2014-0099995 A | 8/2014 |
| KR | 10-2014-0131121 A | 11/2014 |
| WO | 2014-148903 A1 | 9/2014 |

OTHER PUBLICATIONS

Meng Chen et al., "Optical microplates for high-throughput screening of photosynthesis in lipid lipid-producing algae," Lab on a Chip, 2012, vol. 12, pp. 3870-3874.

Ulrich M Tillich et al., "High-throughput cultivation and screening platform for unicellular phototrophs," BMC Microbiology, 2014, vol. 14, pp. 239 (1-13).

Martin Kunze et al., "Minireactor-based high-throughput temperature profiling for the optimization of microbial and enzymatic processes," Journal of Biological Engineering, 2014, vol. 8, pp. 22 (1-18).

Hyun Soo Kim et al., "A microfluidic photobioreactor array demonstrating high-throughput screening for microalgal oil production," Lab on a Chip, 2014, vol. 14, pp. 1415-1425.

International Search Report from International Patent Application No. PCT/KR2016/002079, dated Jul. 25, 2016.

Written Opinion from International Patent Application No. PCT/KR2016/002079, dated Jul. 25, 2016.

\* cited by examiner

【FIG. 1】
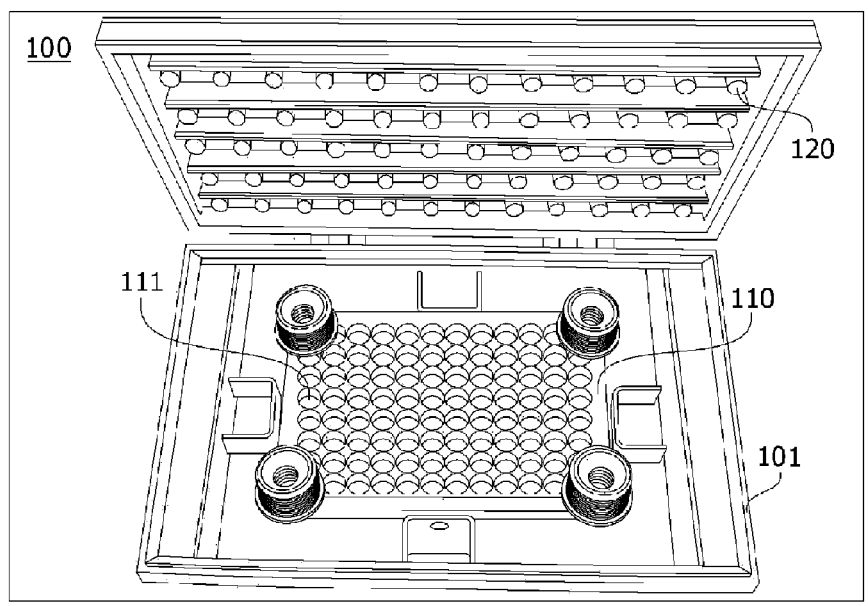
【FIG. 2】
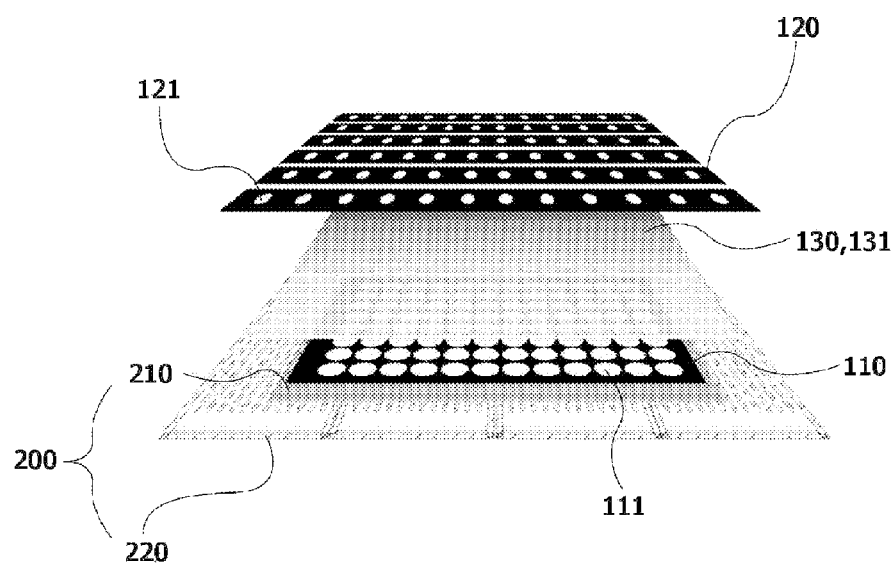

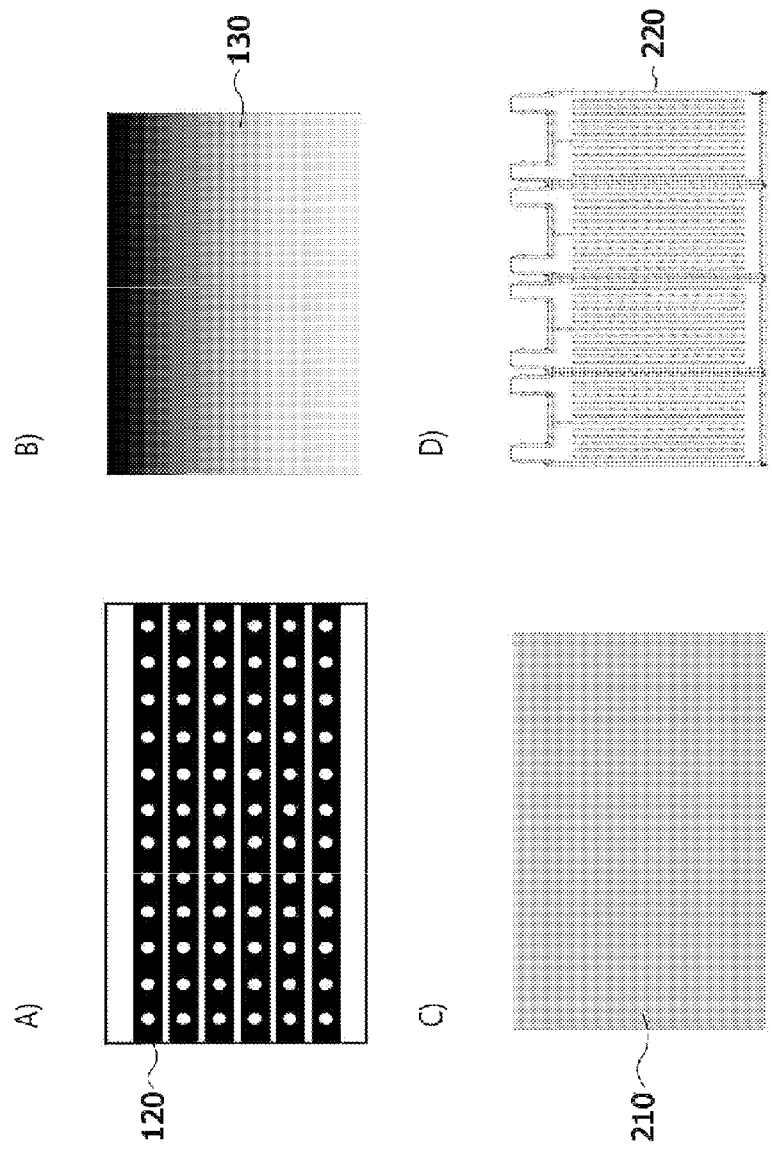

【FIG. 4】
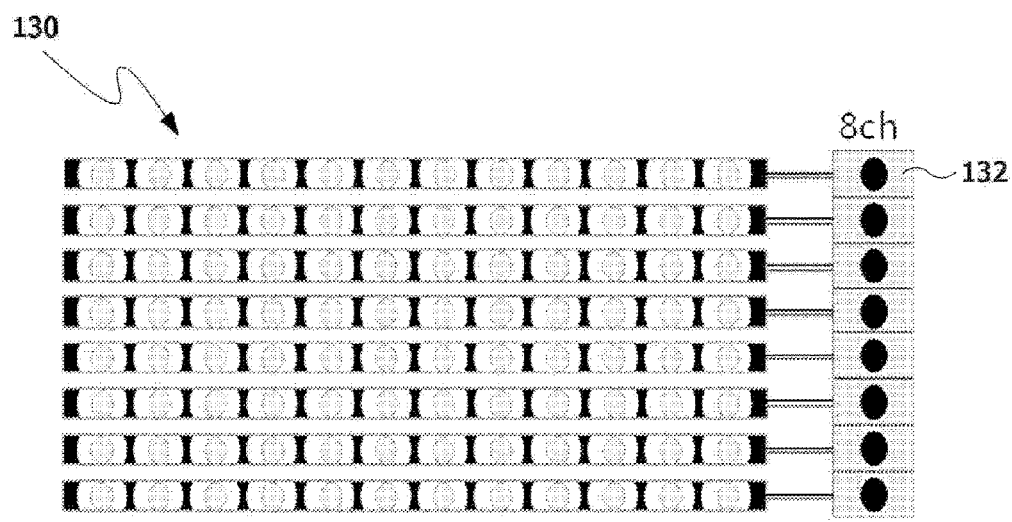
【FIG. 5】
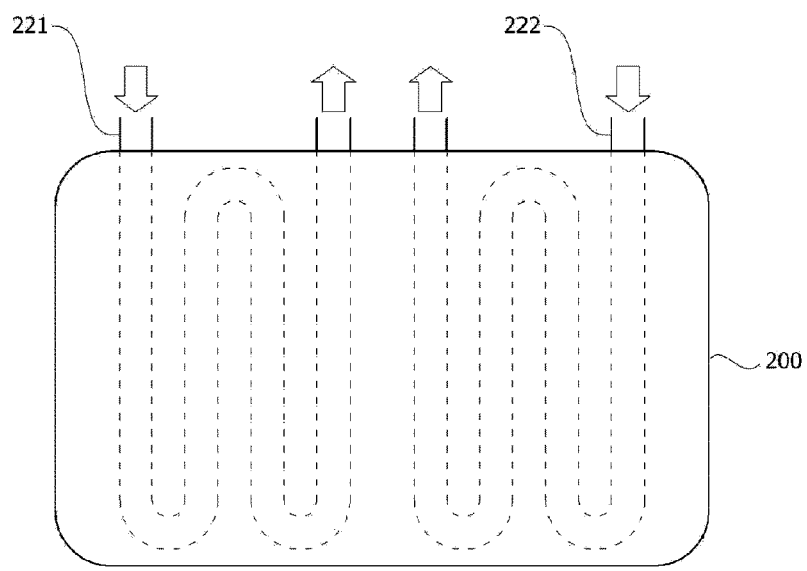

【FIG. 6】
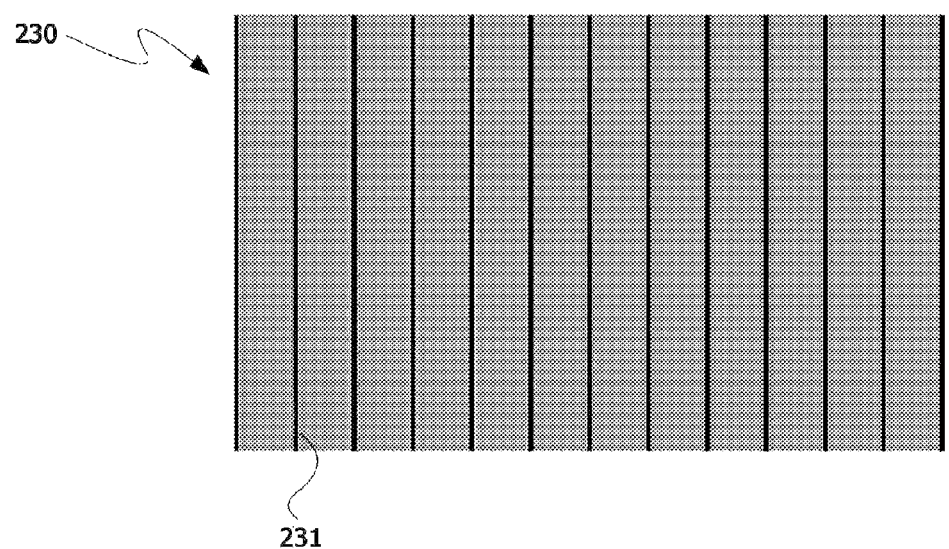

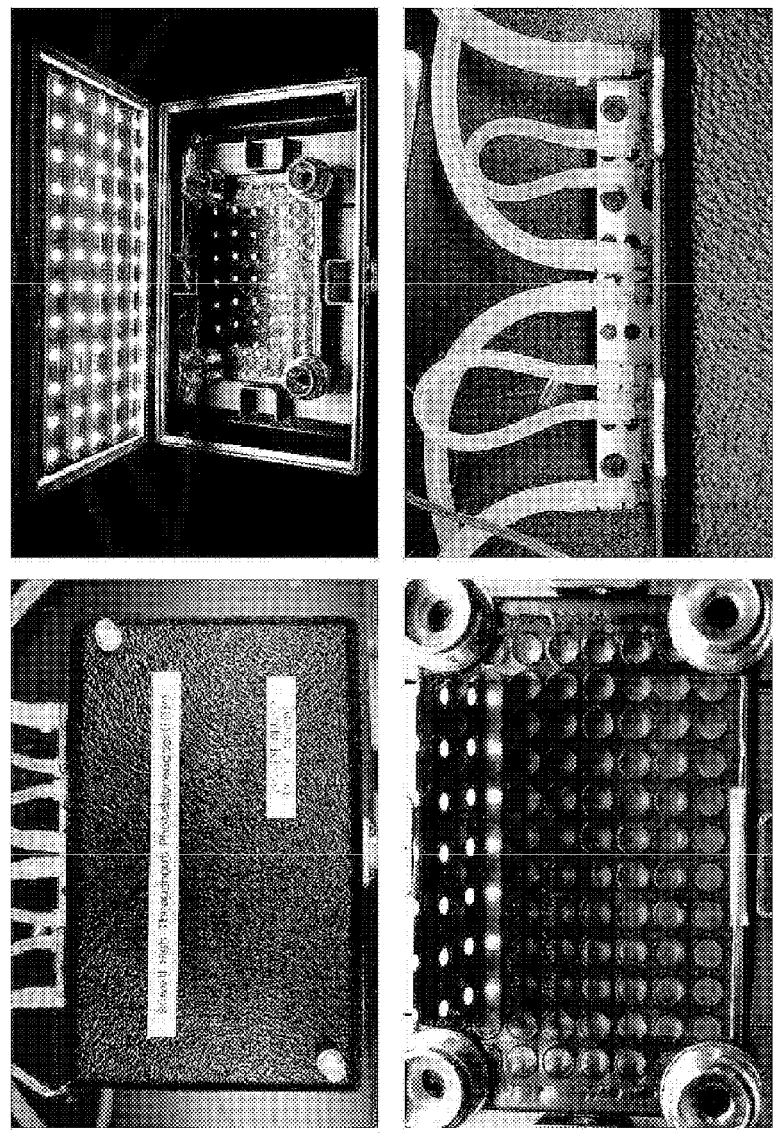
[FIG. 7]

[FIG. 8]
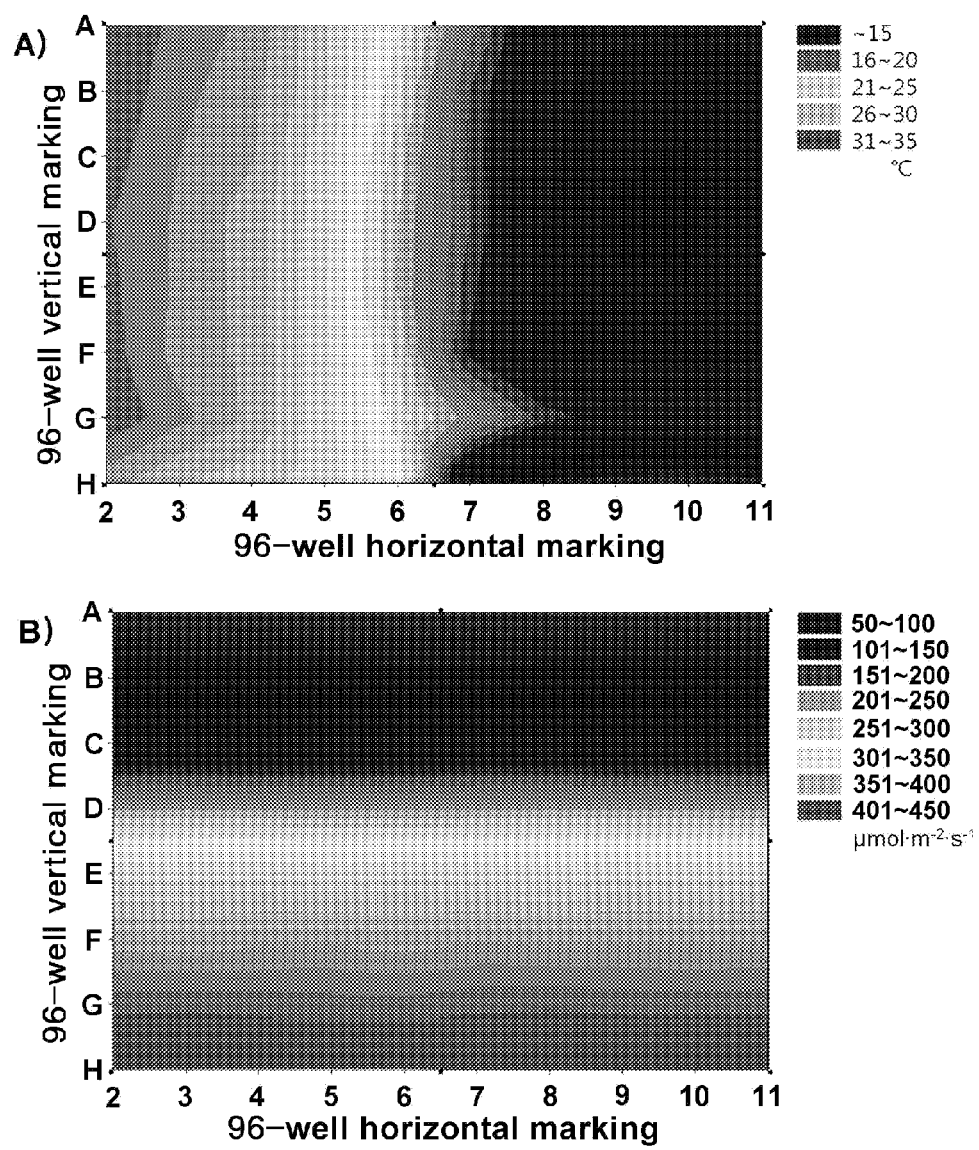

[FIG. 9]
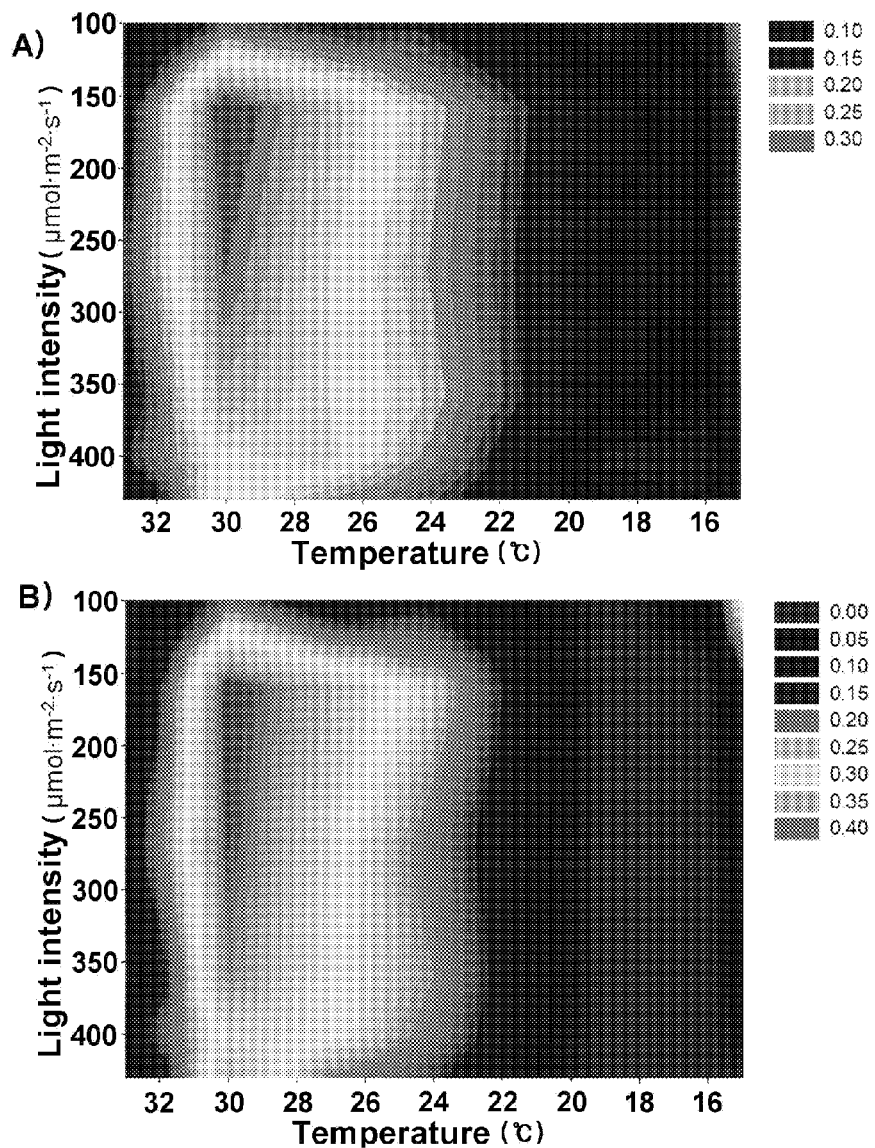

[FIG. 10]
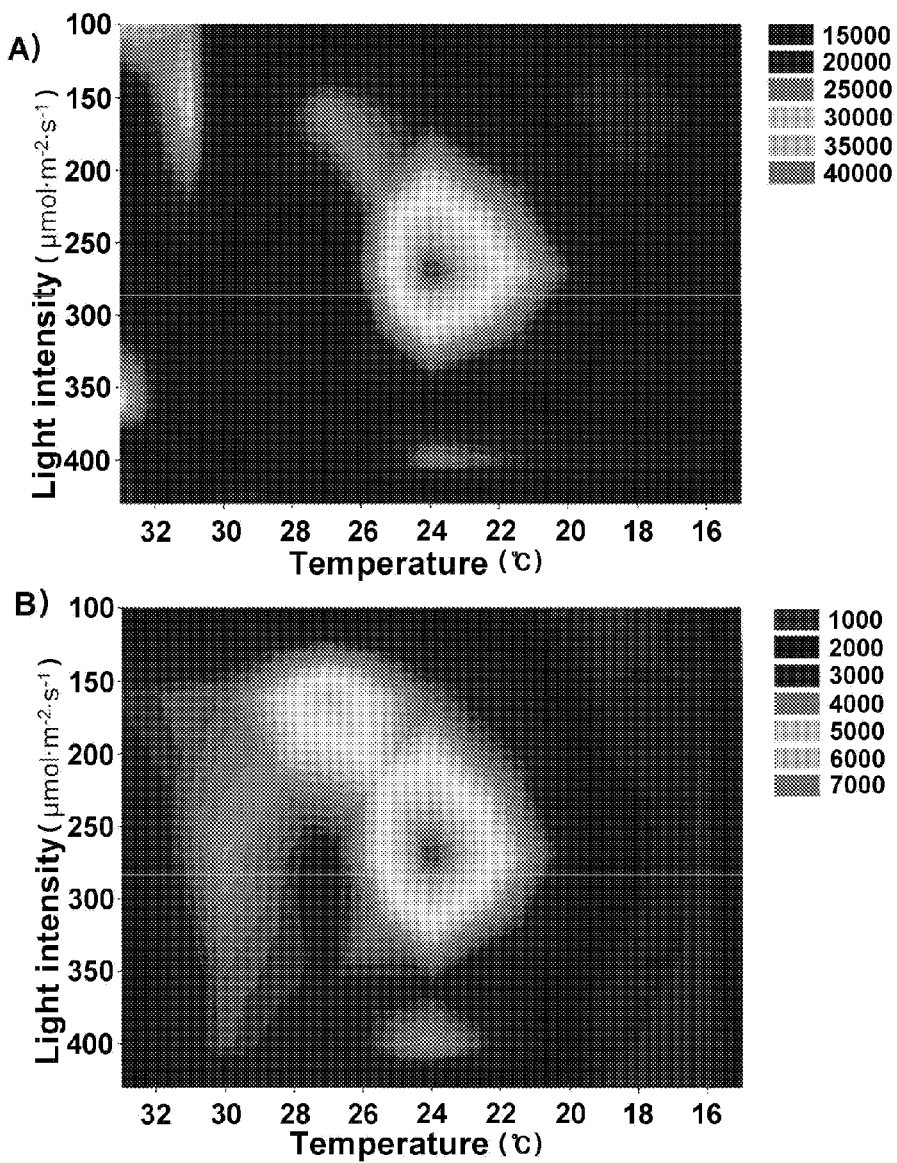

[FIG. 11]
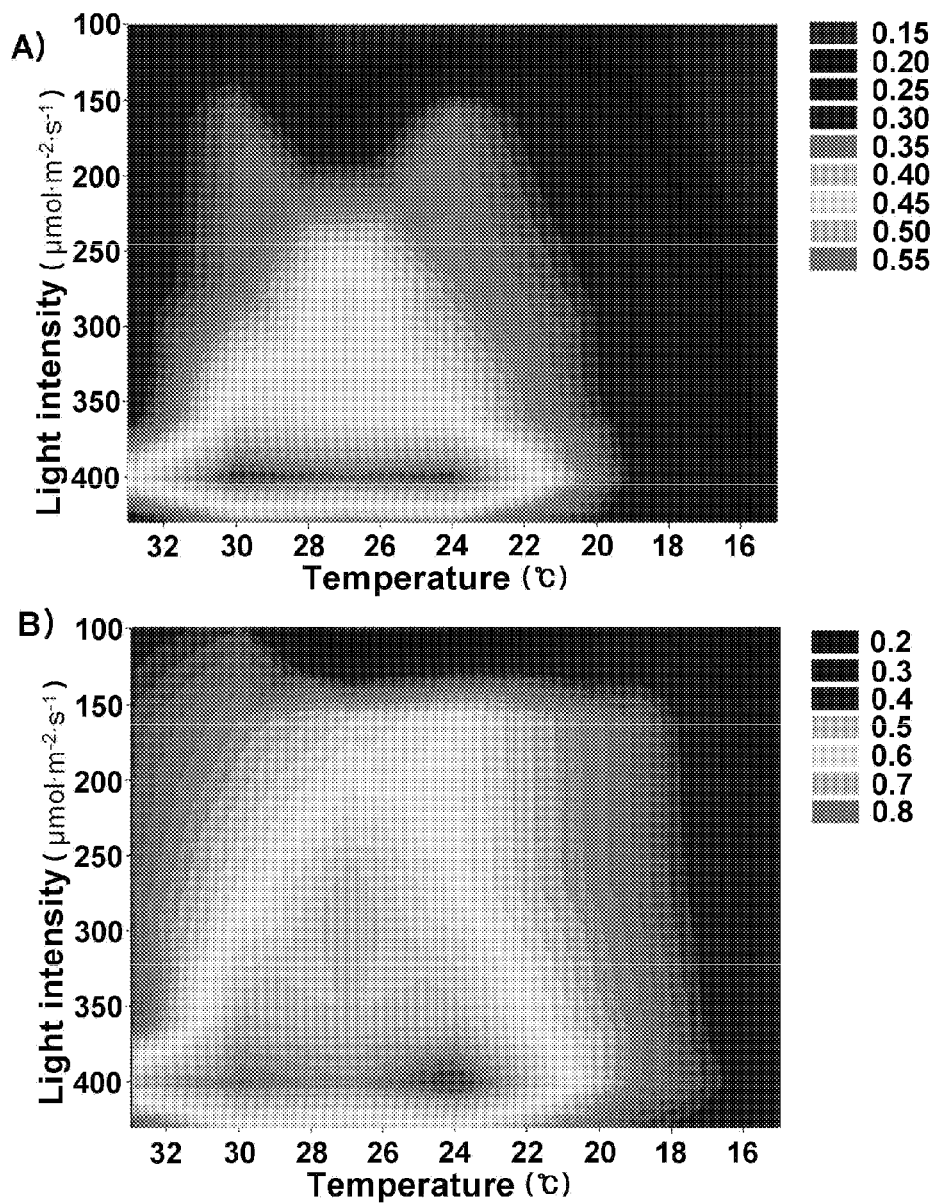

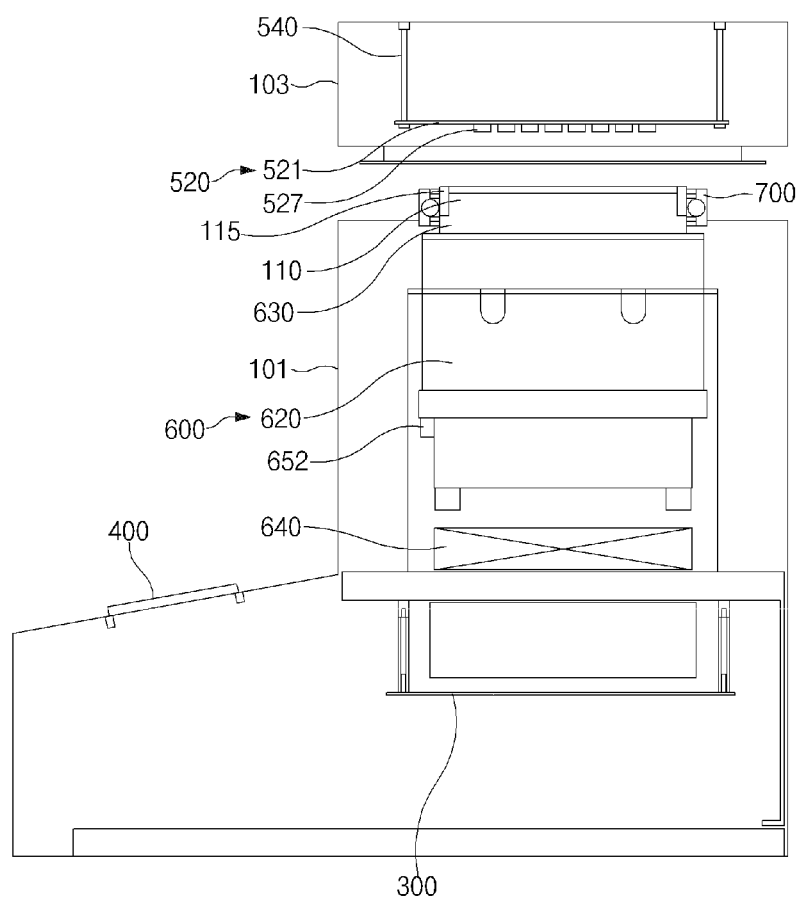
[FIG. 12]

[FIG. 13]
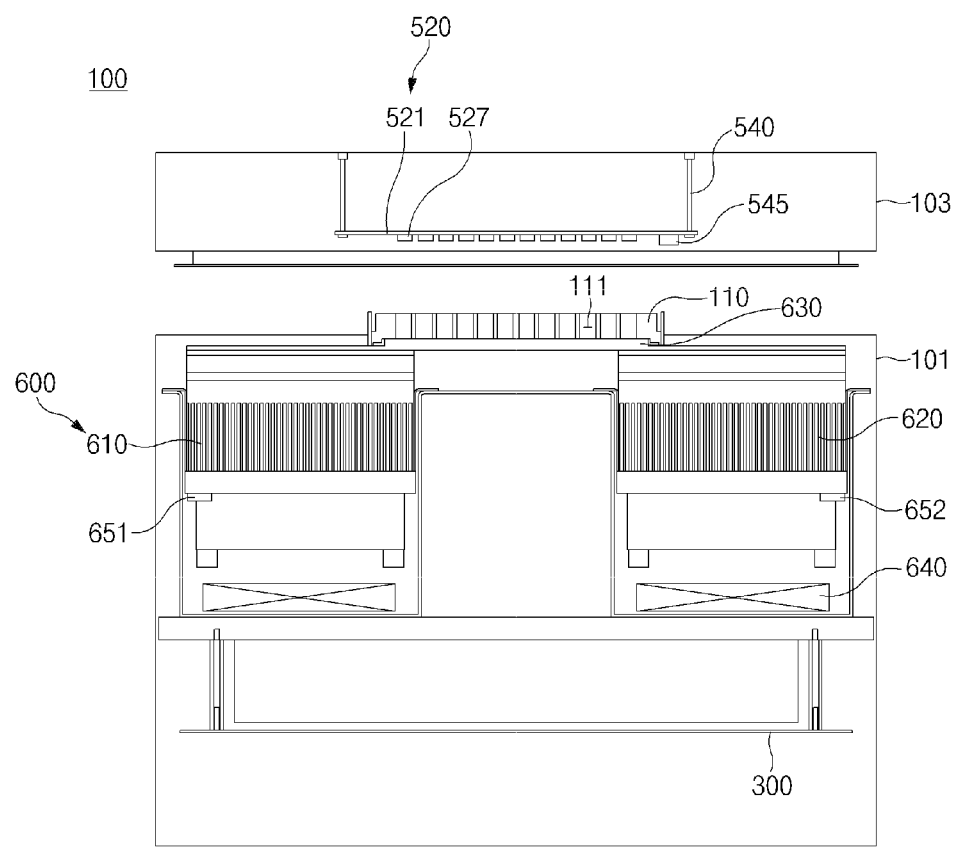

【FIG. 14】
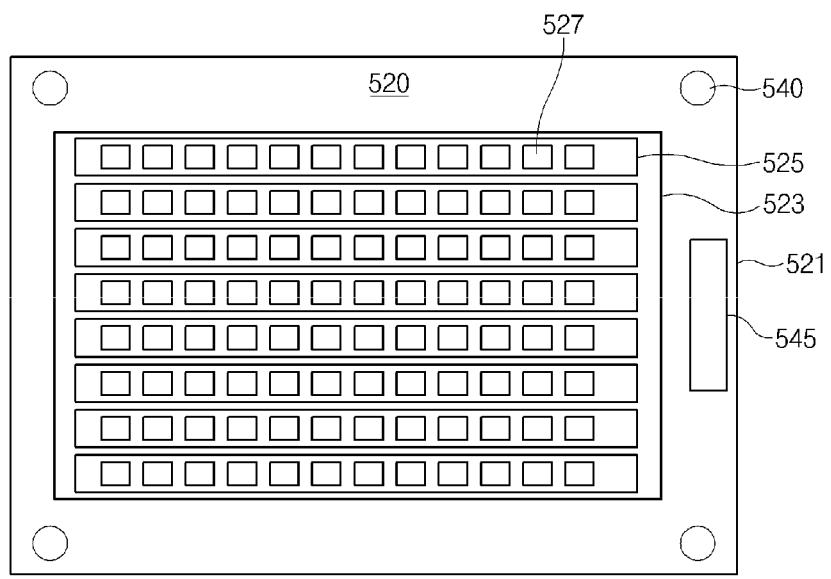
【FIG. 15】
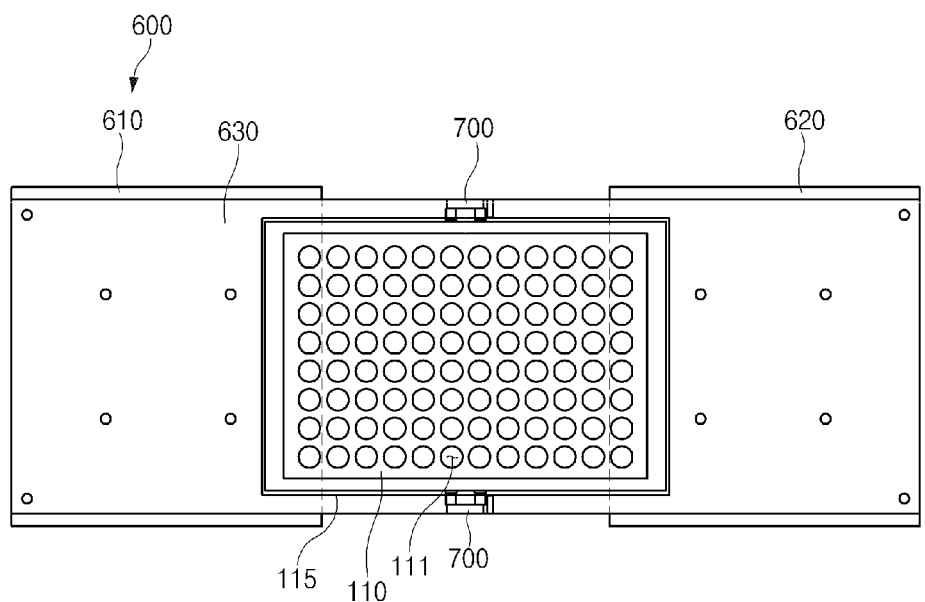

【FIG. 16】
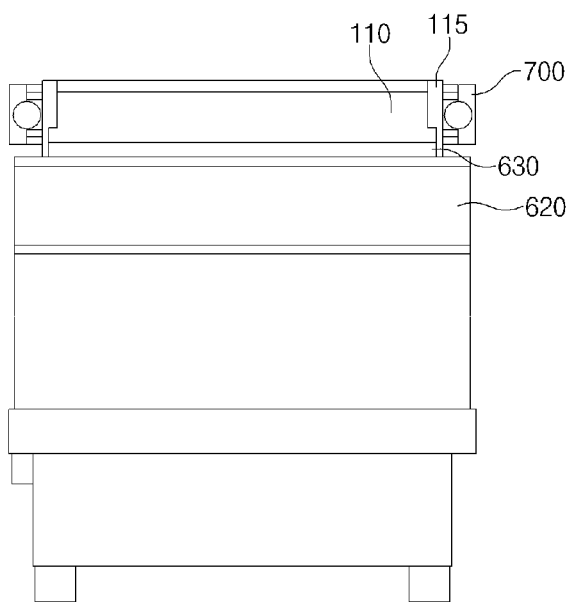

HIGH THROUGHPUT PHOTOBIOREACTOR

This application is a Continuation-in-Part of PCT/KR2016/002079, filed 2 Mar. 2016, which claims benefit of Serial No. 10-2015-0170245, filed 1 Dec. 2015 in the Republic of Korea, and claims benefit of Serial No. 10-2015-0029732, filed 3 Mar. 2015 in the Republic of Korea and which applications are incorporated herein by reference. To the extent appropriate, a claim of priority is made to each of the above disclosed applications.

TECHNICAL FIELD

The present invention relates to a high throughput photobioreactor, and more particularly, to a high throughput photobioreactor capable of culturing photosynthetic microorganisms.

BACKGROUND ART

Global oil crises such as depletion of petroleum and natural gas and instability of supply and demand systems are being created. Restrictions on the use of fossil fuels as energy sources are becoming more visible to protect ecosystems from climate change and environmental destruction or the like.

As a result, all countries of the world are making efforts not only to develop new and renewable energy but also to increase the efficiency of existing thermal power generation and to make eco-friendly inventories. Biological energy production technologies using photosynthetic microorganisms or the like are also attracting attention.

In recent years, research on the use of photosynthetic microorganisms has focused on the production of biofuels for transportation, due to the increase in prices of cereal resources due to the production of biofuels and concerns about food resources. In accordance with this, application researches such as improvement in microorganisms, a reactor, system research or the like in addition to basic researches on genomes and genes of photosynthetic microorganisms or the like have been conducted on a large scale.

The photosynthetic microorganisms can grow using water, carbon dioxide and sunlight, and can be cultivated anywhere in wastelands, coasts, and oceans, such that they do not compete with existing land crops in terms of land or space. The photosynthetic microorganisms accumulate large amounts of lipids (up to 70%) in a living body according to culture conditions and their oil (lipid) production per unit area is 50-100 times higher than typical edible crops such as soybeans, such that they may have very high functionality as biodiesel. The biodiesel, which is produced using the photosynthetic microorganisms such as microalgae as a raw material, can greatly reduce emission of pollutants such as fine dust and sulfur compounds as compared with the conventional diesel fuel and therefore is suitable as fuel for an eco-friendly car.

In order to efficiently produce the photosynthetic microorganisms, development of high-efficiency photobioreactors and high concentration culture techniques has been attempted, and a method for culturing photosynthetic microorganisms such as microalgae can be roughly classified into a method using an outdoor culture method and a method using a photobioreactor.

An example of the outdoor culture method may include a water channel type in which the medium is circulated in a pond shape or an outer wheel shape. The outdoor culture method has less installation cost and operation cost, but has a disadvantage in that it has difficulty in performing the high concentration culture and may be easily contaminated by other microorganisms to increase withdraw cost of photosynthetic products.

Therefore, it becomes possible to produce high value added materials such as biofuels, pharmaceuticals, health foods, and feeds using the photosynthetic microorganisms. In particular, as a high concentration mass culturing technique of photosynthetic microorganisms is essentially required for a biological carbon dioxide immobilization process, a demand for a photobioreactor having high culture efficiency is increasing.

Korean Patent No. 10-0283026 which is currently developed domestically discloses a form of a photobioreactor in which an aerial photobioreactor uses a cylindrical inner conduit as a luminous body and Korean Patent Laid-open Publication No. 10-2003-0018196 discloses a cylinder type photobioreactor in which an agitator is used as a luminous body.

Isolation of high productivity microalgae and establishment of optimal production conditions by the photobioreactors are essential for increasing biomass productivity. The productivity of microalgae greatly depends on conditions of a quantity of light, temperature and carbon dioxide. The isolation of the microalgae having high productivity and the optimal culture conditions should take into account the essential requirements of the photosynthesis, but it is not easy to control the conditions of the quantity of light, the temperature, and the carbon dioxide in the laboratory environment.

Accordingly, there is a need for a photobioreactor capable of establishing optimal production conditions.

DISCLOSURE

Technical Problem

An object of the present invention is to provide a high throughput photobioreactor for establishing optimal production conditions by constructing various wide ranges of temperature conditions to cultivate microorganisms in various environments.

Another object of the present invention is to provide a high throughput photobioreactor capable of more precisely setting optimal conditions necessary for production of microalgae and enabling even by unskilled researchers to easily and conveniently control a quantity of light and temperature.

Technical Solution

In one general aspect, a high throughput photobioreactor includes: a chamber; a plate installed in the chamber and mounted with a plurality of wells; a plurality of light sources installed in the chamber and irradiating light toward the plate; a light quantity controller positioned on an upper part of the plate to make quantities of light irradiated to the plurality of wells different; and a temperature controller controlling a temperature of the plate.

The light source may be included in the chamber and may be at least one of a light emitting diode (LED) and organic light emitting diodes (OLEDs).

The light quantity controller may be a light quantity control film that is disposed between the plate and the light source and has a gradation.

The light quantity control film may be formed to have a gradation at which a color is getting more transparent from an achromatic color from one side toward the other side in a longitudinal direction.

The light quantity control film may be formed to have a gradation at which a color is getting more transparent from a chromatic color from one side toward the other side in a longitudinal direction.

The light quantity controller may be a dimmer connected to the light source to control a supply amount of current to control brightness of the light source.

The plurality of light sources may be formed in at least two groups which are longitudinally disposed to be spaced from each other and at least two dimmers may be provided to be connected to the light sources of the groups to control the quantities of light to be different according to each group.

The temperature controller includes: a temperature control block including a first temperature control pipe positioned at a lower part of the plate and injected with hot water or heated air to control a temperature of the plate and a second temperature control pipe injected with cooling water or cooling air to control a temperature of the plate; and a temperature diffusion plate positioned between the temperature control block and the plate to keep the temperature of the plate.

The first temperature control pipe and the second temperature control pipe may be disposed to be spaced apart from each other in a lateral direction.

The temperature controller may include: a plurality of semiconductor elements extending in a longitudinal direction of the plate; and a temperature control device heating or cooling the semiconductor element to control the temperature of the plate, in which the plurality of semiconductor elements may be disposed to be spaced apart from each other in a lateral direction.

The high throughput photobioreactor may further include: a controller controlling the quantity of light of the light quantity controller and the temperature of the temperature controller; and a monitor receiving a signal about the temperature and the quantity of light from the controller and visually displaying the signal and receiving setting of a user for the control of the controller.

The temperature controller may include: a first thermo electric cooling (TEC) module heated or cooled at a temperature input by the controller; a second TEC module installed to be spaced apart from the first TEC module and receive a temperature higher than that of the first TEC module by the controller; and a plate-like temperature gradient block installed so that an upper surface thereof comes into surface contact with a lower surface of the plate, and a lower surface of one side thereof comes into contact with the first TEC module and a lower surface of the other side thereof comes into contact with the second TEC module to allow the first TEC module and the second TEC module to heat or cool both ends thereof at different temperatures, thereby forming a temperature gradient, in which the temperature of the plate may be controlled while the temperature gradient is generated in the well in a lateral direction by a temperature difference between the first TEC module and the second TEC module.

The temperature controller may further include a temperature sensor attached to the first TEC module and the second TEC module to detect the temperature.

The controller may finely raise or lower the temperature of the first TEC module and the second TEC module by a pulse width modulation (PWM) control.

The light source may be provided in the chamber and may be configured to include a printed circuit board (PCB) on which a predetermined circuit pattern is formed and an LED substrate portion that includes an LED module in which a plurality of LED units configured of a plurality of LED elements disposed on the PCB and having the same quantity of light are arranged in a longitudinal direction, and the light quantity controller may be configured so that the plurality of LED units generate different quantities of light by an electronic control of the controller to form a light gradient in the LED module in a longitudinal direction.

The LED substrate portion may be detachably to the chamber to be replaced with various kinds of light sources.

Advantageous Effects

According to the high throughput photobioreactor according to an embodiment of the present invention, it is possible to establish the optimal production conditions by constructing various wide ranges of temperature conditions to cultivate the microorganisms in various environments.

On the other hand, if the high throughput photobioreactor according to another embodiment of the present invention is used, the controller for electronically controlling the temperature and the quantity of light and the monitor connected to the controller can be more precisely set the optimal conditions necessary for the production of microalgae and even by the unskilled researchers can easily and conveniently control the quantity of light, the temperature, or the like.

In addition, according to another embodiment of the present invention, since the wide range of temperature environment can be easily set, it is possible to efficiently cultivate various types of microalgaes.

In addition, according to another embodiment of the present invention, since the LED substrate portion is replaceably provided, the LED light suitable for the cultured photobiology can be applied to further increase the culture efficiency.

BRIEF DESCRIPTION OF THE DRAWINGS

FIG. 1 is a view showing a photobioreactor according to an embodiment of the present invention.

FIG. 2 is an exploded perspective view of the photobioreactor according to the embodiment of the present invention.

FIG. 3 is a configuration view of the photobioreactor according to the embodiment of the present invention.

FIG. 4 is a view showing a light quantity controller of the photobioreactor according to the embodiment of the present invention.

FIG. 5 is a view showing a temperature controller of the photobioreactor according to the embodiment of the present invention.

FIG. 6 is a view showing the temperature controller of the photobioreactor according to the embodiment of the present invention.

FIG. 7 is a photograph of the photobioreactor according to the embodiment of the present invention.

FIG. 8 is a graph showing a temperature gradient and a light gradient of the photobioreactor according to the embodiment of the present invention.

FIG. 9 is a graph showing optimal growth conditions when *P. kessleri* JD076 was cultured by the photobioreactor of the present invention ((A) optical density value and (b) growth rate).

FIG. 10 is a graph showing optimal conditions for neutral lipid production when the *P. kessleri* JD076 was cultured in an air feed culture using the photobioreactor of the present invention ((A) nile red intensity per unit cell, (B) neutral lipid productivity).

FIG. 11 is a graph showing the optimal growth conditions when the *P. kessleri* JD076 was cultured under a supply of 5% of $CO_2$ ((A) optical density value and (B) growth rate).

FIG. 12 is a side view of a photobioreactor according to another embodiment of the present invention.

FIG. 13 is a front view of a photobioreactor according to another embodiment of the present invention.

FIG. 14 is a bottom view of an example of a light source applied to another embodiment of the present invention.

FIG. 15 is a top view of a plate and a temperature controller applied to another embodiment of the present invention.

FIG. 16 is a right side view of FIG. 15.

BEST MODE

Hereinafter, embodiments of the present invention will be described in detail with reference to the accompanying drawings.

First, the embodiments described below are examples suitable for understanding technical characteristics of the high throughput photobioreactor of the present invention. However, the technical features of the present invention are not limited to the embodiments of the present invention to be described below, and various modifications can be made within the technical scope of the present invention.

The present invention relates to a high throughput photobioreactor capable of culturing photosynthetic microorganisms in various environments by constructing various wide ranges of temperature conditions in a single culture.

According to the present invention, the photosynthetic microorganism may mean green algae, red algae, and blue algae capable of photosynthesis, and may include chlorella, chlamydomonas, haematococous, botryococcus, scenedesmus, spirulina, tetraselmis, dunaliella, or the like but are not limited thereto. At this time, the microalgae described above can produce carotenoids, cells, pycobiliproteins, lipids, carbohydrates, unsaturated fatty acids, and proteins in a culture container.

A photobioreactor 100 according to an embodiment of the present invention will be described with reference to FIGS. 1 to 11.

Referring to FIGS. 1 to 7, a high throughput photobioreactor 100 according to the embodiment of the present invention includes a chamber 101, a plate 110 installed inside the chamber 101, a plate 110 on which a plurality of wells 111 are mounted, a light source 120 installed in the chamber 101 to irradiate light toward the plate 110, a light quantity controller 130 disposed between the plate 110 and the light source 120 to make the quantity of light irradiated to the plurality of wells 111 different, and a temperature controller 200 for controlling the temperature of the plate 110.

First, the chamber 101 is typically provided with a receiving space having a predetermined size therein, and may be provided with a door that can open and close the inside of the chamber 101. A plate 110 is mounted in the chamber 101 in which the light source 120, the light quantity controller 130, the temperature controller 200 or the like may be mounted.

In addition, one frame of the plate 110 may be provided with the plurality of wells 111 each of which may be aligned to efficiently detect various types of information. FIG. 1 illustrates an example in which 96 wells 111 are mounted. However, four, eight, sixteen, and twenty four wells 111 or the like may be used depending on the desired culture purpose.

At this time, the well 111 may have any shape such as a square column, a cylinder, a rhombic column, and a test tube type as long as it can contain liquid, and may have a shape of a square column or a cylinder having a flat bottom for optical detection.

In addition, light necessary for the growth of photosynthetic microorganisms can be irradiated from the light source 120 installed in an upper part of the chamber 101. At this time, the light source 120 may be a light emitting diode (LED) or an organic light emitting diode (OLED). In particular, the light sources 120 may be operated by using one type of light source 120 or by two or more types of light sources 120 in combination.

In addition, the photobioreactor 100 according to the embodiment of the present invention can be variously constructed in a wide range by a single culture. Here, a light quantity control film 131 is provided between the plate 110 and the light source 120, such the quantity of light transmitted to each of the wells 111 can be controlled differently.

More specifically, the light quantity control film 131 may be formed to have a gradation in transparency or hue from one side toward the other side. For example, the light quantity control film 131 may be formed to have a gradation that is getting more transparent from an achromatic color from one side toward the other side and may be formed to have a gradation that is getting more transparent from dark gray from one side toward the other side. As another aspect, the light quantity control film 131 can be formed to have a gradation that is getting more transparent from a chromatic color from one side to the other side.

Here, the term achromatic color means the collective term of a colorless object color ranging from white to gray through black, and the term chromatic color means colors with hue among object colors. The chromatic color can be red, green, blue, purple, etc.

For example, it may be formed to have a gradation that is getting more transparent from red from one side toward the other side, and have a gradation that is getting more transparent from blue.

Such a light quantity control film 130 may be a film printed to have a gradation effect using specific paint.

As a specific aspect, referring to FIG. 4, the light quantity controller 130 may be a dimmer 132 for controlling the quantity of light of the light source 120 to be different. More specifically, the plurality of light sources 110 may be formed in at least two groups which are longitudinally disposed to be spaced from each other, and at least two dimmers 132 are provided to be connected to the light sources 120 of the groups to control the quantity of light to be different according to each group. The light source 110 may be formed in, for example, eight groups, in which the quantities of light of the eight groups may be controlled to be different from each other.

That is, the amount of current supplied to each light source can be controlled by the dimmer 132 to control the brightness of the light source.

On the other hand, the temperature controller 200 includes a temperature control block 220 and a temperature diffusion plate 210 and may use the temperature diffusion plate 210 and the temperature control block 220 for a temperature control to keep the temperature in the chamber 101 constant.

In particular, the temperature control block 220 may include a first temperature control pipe 221 and a second temperature control pipe 222. That is, the temperature control block 220 can consist of a water circulation system including a plurality of circulating pipes and circulate water at a predetermined temperature to control the temperature of the plate 110 in various ways.

More specifically, hot water or heated air can be injected into the first temperature control pipe 221 to control the temperature of the plate 110, and cold water or cool air can be injected into the second temperature control pipe 222 to control the temperature of the plate 110. At this time, the hot air or the heated air injected into the first temperature control pipe 221 may range from 30 to 50° C., and the cold water or the cool air injected into the second temperature control pipe 222 may range from 4 to 15° C.

In particular, a non-growth rate of microorganisms is greatly influenced by the environment in which the microorganisms grow, particularly by the culture temperature. The photobioreactor 100 needs to be maintained at a temperature suitable for the growth and production of microorganisms, and a heat transfer phenomenon and a temperature control in the photobioreactor are important factors for determining the characteristics and efficiency of the photobioreactor.

According to the embodiment of the present invention, the photobioreactor 100 is controlled by injecting hot water and cooling water using the temperature control block 220 and, a temperature of a culture liquid of the photobioreactor 100 can be kept substantially constant by the temperature diffusion plate 210.

On the other hand, referring to FIG. 6, the temperature controller 200 may include a semiconductor element 231. More specifically, the temperature controller 200 may be configured to include a plurality of semiconductor elements 231 extended in a longitudinal direction and a temperature controller (not shown) controlling the temperature of the plate 110 by heating or cooling the semiconductor element 231, in which the semiconductor element 231 may can be spaced apart from each other in a lateral direction to control the temperature, like the temperature control block 220.

In addition, the photobioreactor 100 of the present invention may further include a gas supplier for supplying carbon dioxide into the chamber 101, in which the gas supplier may include a supply pipe connected to the chamber 101 and a supply pump installed on one side of the supply pipe and perform pumping to supply the carbon dioxide into the chamber 101.

An additional detection method may be performed in the photobioreactor 100 of the present invention in order to detect various kinds of information of the photosynthetic microorganisms cultured in the well 111 on a bottom of each well 111. For example, dissolved oxygen, carbon dioxide, pH, etc. in the well 111 can be monitored by the additional detection method.

Hereinafter, in order to facilitate understanding of the present invention, experimental examples will be described in detail. It is to be understood, however, that the following experimental examples are only illustrative of the content of the present invention and the scope of the present invention is not limited to the following experimental examples. The experimental examples are provided so that this disclosure will be thorough and complete, and will fully convey the concept of the invention to those skilled in the art.

EXPERIMENTAL EXAMPLE

Experimental Example 1. Photosynthetic Microorganism and Culture Condition

In the present experiment example, for a culture of photosynthetic microorganisms using the photobioreactor 100, parachlorella (parachlorella sp. JD076) strain was used and BG11 medium was used. The BG11 medium was prepared by mixing Stock No. 1 to Stock No. 9 disclosed in the following Table 1. At this time, $K_2HPO_4$, ammonium ferric citrate, and a trace metal solution were separately sterilized and added after the medium is sterilized. In particular, the trace metal solution was mixed with $H_3BO_3$, $MnCl_24H_2O$, $ZnSO_47H_2O$, $Na_2MoO_4.2H_2O$, $CuSO_45H_2O$, and $Co(NO_3)_2.6H_2O$ as shown in Table 1 below and diluted by taking 1 ml per 1 L.

TABLE 1

| Stock No. | Medium ingredient | Content |
|---|---|---|
| 1 | $NaNO_3$ | 15 g/L |
| 2 | $K_2HPO_4$ | 0.04 g/L |
| 3 | $MgSO_4•7H_2O$ | 0.075 g/L |
| 4 | $NaCO_3$ | 0.0202 g/L |
| 5 | $CaCl_2•2H_2O$ | 0.006 g/L |
| 6 | Citric acid | 0.006 g/L |
| 7 | Ammonium ferric citrate | 0.006 g/L |
| 8 | $Na_2•EDTA$ | 0.001 g/L |
| 9 | Trace metal solution | |
| | $H_3BO_3$ | 2.86 g/L |
| | $MnCl_24H_2O$ | 1.81 g/L |
| | $ZnSO_4•7H_2O$ | 0.22 g/L |
| | $Na_2MoO_4•2H_2O$ | 0.39 g/L |
| | $CuSO_4•5H_2O$ | 0.08 g/L |
| | $Co(NO_3)_2•6H_2O$ | 0.05 g/L |

In addition, the LED lamp was used as the light source, the quantity of light was measured by a Li-COR (Li-198) light meter (Li-COR, USA), and the temperature of each well was measured by an IR thermometer (FLUKE, USE). The measurement was repeated three times to obtain an average value, and the temperature gradient and the light gradient generated in each well were as shown in FIG. 8. The temperature was in the range of 15 to 33° C. and light was in the range of 4 to 450 $\mu mol/m^2/s$.

In addition, the cell concentration (OD) was 0.1, and the wells were filled with 200 µl at the same concentration. The cell was cultured for 2 days in the state in which it is not injected with $CO_2$ and 2 days in after it is injected with 5% of $CO_2$. After the culturing, the optical density of a cell biomass was measured by a microplate absorbance reader (Tecan, Switzerland), and the nile red intensity of a cell biomass was measured by a microplate fluorescence reader (Biotek, USA).

Experimental Example 2. Optimal Conditions for Growth of Photosynthetic Microorganisms In the above Experimental Example 1, *parachlorella kessleri* (JD076) was cultured by the photobioreactor 100. In the present experiment example, after the culturing, the optical density, the cell biomass, the neutral lipid content, or the like were measured.

FIG. 9 is a graph showing the optical density A and the growth rate B when *P. kessleri* JD076 was cultured by the photobioreactor 100 of the present invention. Referring to FIG. 9, if the photobioreactor 100 was not supplied with air (no $CO_2$ was injected), it could be confirmed that the cell biomass of the *parachlorella kessleri* (JD076) was increased to a maximum of 0.3.

In particular, in the section where the cell biomass is increased, the optimal section was the temperature range of 29 to 30° C. and the light condition was optimized in 150 to 250 µmol/m²/s. In particular, it could be confirmed that such a result was similarly analyzed even in the result obtained by converting the optical density value into the growth rate, and the maximum growth rate was 0.4/day.

FIG. 10 is a graph showing optimal conditions for neutral lipid production when the *P. kessleri* JD076 was cultured in an air feed culture using the photobioreactor 100 of the present invention ((A) nile red intensity per unit cell, (B) neutral lipid productivity).

Referring to FIG. 10, the intracellular neutral lipid content was confirmed through nile red dye. As a result, it was confirmed that the section where the neutral lipid was maximally stored in the cell has the condition that the temperature is 24° C. and the quantity of light is 280 µmol/m²/S.

FIG. 11 is a graph showing the optimal conditions when the *P. kessleri* JD076 was cultured under a supply of 5% of $CO_2$ ((A) optical density value and (B) growth rate).

Referring to FIG. 11, it could be confirmed that the optimal culture section was 24 to 30° C. and the light condition was 400 µmol/m²/s in the culture environment containing 5% of $CO_2$. In addition, the optical density value and the growth rate of the cell mass were higher when $CO_2$ was supplied than when $CO_2$ was not supplied. More specifically, it was confirmed that the cell biomass was 0.55 and the growth rate was 0.8/day.

In other words, when *P. kessleri* JD076 was cultured using the photobioreactor 100 of the present invention, the change in the cell biomass could be confirmed could be confirmed only in four days according to temperature, light, and absence and presence of $CO_2$, and the lipid content analysis by the nile red dye could confirm the optimal culture conditions of microorganisms.

Hereinafter, a high throughput photobioreactor 100 according to another embodiment of the present invention will be described with reference to FIGS. 12 to 16.

The high throughput photobioreactor 100 according to another embodiment shown in FIGS. 12 to 16 is different from the embodiment shown in FIGS. 1 to 11 in a light source 520, a light quantity controller, and a temperature controller 600 and in that it further includes a vibrator 700. Therefore, the detailed description of the same configuration as that of the above embodiment will be omitted.

As the embodiment shown in FIG. 12, the high throughput photobioreactor 100 according to another embodiment of the present invention includes a controller 300 controlling the quantity of light of the light quantity controller 130 and the temperature of the temperature controller 600 and a monitor 400 receiving signals about the temperature and the quantity of light from the controller 300 and visually displaying the signals and receiving user settings for controlling the controller 300.

The controller 300 may control the quantity of light of the light quantity controller 130 and the temperature of the temperature controller 600 to be controlled to a predetermined value.

For example, the controller 300 may be configured of a main board having a main controller (hereinafter, referred to as MCU) installed in the chamber 101 as a main controller. The light source 520, the light quantity controller 130, and the temperature controller 600 are electrically connected to the MCU so that the temperature and the quantity of light can be controlled by the MCU.

However, the controller 300 is not limited to the embodiment illustrated and the example described above, and may be variously modified as long as it is electrically connected to the light quantity controller 130 and the temperature controller 600 to control the temperature and the quantity of light.

On the other hand, the monitor 400 can receive signals about the temperature and the quantity of light from the controller 300 and visually display the signals, and receive the user setting for the control of the controller 300.

For example, the monitor 400 may be configured as a touch screen so that the user can easily confirm information and input information. The monitor 400 can be connected to the controller 300 provided as the MCU to confirm the information on the quantity of light and the temperature in real time and easily set the proper temperature.

Specifically, the current temperature and the expected temperature by the setting can be displayed on the touch screen. The current intensity of the LED provided as the light source 520 can be confirmed and the desired intensity can be set. However, the monitor 400 is not limited to the above-described embodiment, and may be variously modified as long as it receives and displays the signal from the controller 300 and the user can input necessary information.

If the high throughput photobioreactor 100 according to another embodiment of the present invention is used, the controller 300 for electronically controlling the temperature and the quantity of light and the monitor 400 connected to the controller 300 can be more precisely set the optimal conditions necessary for the production of microalgae and even by the unskilled researchers can easily and conveniently control the quantity of light, the temperature, or the like.

Meanwhile, describing the embodiment with reference to FIGS. 12 and 13, the temperature controller 600 according to another embodiment of the present invention includes a first thermo electric cooling (TEC) module 610 heated or cooled at a temperature input by the controller 300, a second TEC module 620 installed to be spaced apart from the first TEC module 610 and receiving a temperature higher than that of the first TEC module 610, a plate-like temperature gradient block 630 installed so that an upper surface thereof comes into surface contact with a lower surface of the plate 110 and a lower surface of one side thereof comes into contact with the first TEC module 610 and a lower surface of the other side thereof comes into contact with the second TEC module 620 to allow the first TEC module 610 and the second TEC module 620 to heat Or cool both ends thereof at different temperatures, thereby forming a temperature gradient, and a controller 300 controlling the temperature of the first TEC module 610 and the second TEC module 620.

The temperature of the plate 110 can be controlled while a temperature gradient is generated in the lateral direction of the well 111 due to a temperature difference between the first TEC module 610 and the second TEC module 620.

Specifically, the temperature gradient block 630 may be formed in a plate shape, and the upper surface thereof may be in surface contact with the whole of the lower surface of the plate 110, and a part of the lower surface thereof may be installed to be in contact with the first TEC module 610 and the second TEC module 620. Further, the temperature gradient block 630 is made of a material having good thermal conductivity to transfer the temperature of the first TEC module 610 and the second TEC module 620 to the plate 110, thereby heating or cooling the well 111 of the plate 110.

At this time, the first TEC module 610 may be heated or cooled to the temperature received by the controller 300. The second TEC module 620 is installed to be spaced apart from the first TEC module 610 and the temperature higher than that of the first TEC module 610 may be input by the controller 300. A cooling fan 640 capable of inducing a flow of air when cooling the first TEC module 610 and the second TEC module 620 is provided in the chamber 101 and can be provided with an inlet and an outlet of air (not shown).

In addition, the temperature gradient block 630 has a lower surface of one side be in contact with the first TEC module 610 and a lower surface of the other side be in contact with the second TEC module 620 so that the first TEC module 610 and the second TEC module 610 heat or cool both ends thereof at different temperatures, thereby forming a temperature gradient in a lateral direction.

That is, only the both ends of the temperature gradient block 630 are in contact with the first TEC module 610 and the second TEC module 620 so that one end of the temperature gradient block 630 becomes the same temperature as the first TEC module 610 and the other end thereof becomes the same temperature as the second TEC module 620, and the temperature gradient block 630 in an area corresponding to the space between the first TEC module 610 and the second TEC module 620 (see FIG. 13) can form a temperature gradient in a lateral direction.

Accordingly, the well 111 mounted on the plate 110 comes into surface contact with the temperature gradient block 630 and receives the temperature, so that the temperature gradient may be generated in the lateral direction. Accordingly, the plurality of wells 111 can have various temperature conditions within the temperature range between the first TEC module 610 and the first TEC module 610.

As illustrated embodiment, the TEC module applied to the temperature controller 600 according to another embodiment of the present invention is disposed in plural by thinly forming a thermoelectric element and the first TEC module 610 and the second TEC module 620 are disposed to be spaced apart from each other at a proper interval, such that the temperature of the low temperature area can be set. Accordingly, the photobioreactor 100 according to another embodiment of the present invention can easily set a wide range of temperature environment, such that various kinds of microalgaes can be cultured.

Meanwhile, the temperature controller 600 may further include temperature sensors 651 and 652 attached to the first TEC module 610 and the second TEC module 620 to sense temperature.

The temperature sensors 651 and 652 can be attached to the first TEC module 610 and the second TEC module 620, respectively and can detect the temperature of the first TEC module 610 and the second TEC module 620 to transmit a signal to the controller 300. The controller 300 can transmit the temperature information received from the temperature sensors 651 and 652 to the monitor 400 and the user can confirm the current temperature in real time through the monitor 400.

On the other hand, the controller 300 can finely raise or lower the temperatures of the first TEC module and the second TEC module by a pulse width modulation (PWM) control.

That is, the temperature signal received by the controller 300 provided as the MCU is converted into the PWM signal and output, such that the temperature of the first TEC module and the second TEC module can be raised or lowered slowly (for example, 0.1° C./sec).

Referring to the embodiments described with reference to FIGS. 13 and 14, the light source 520 may be included in the chamber 101 and configured to include a printed circuit board (PCB) on which predetermined circuit patterns are formed and an LED substrate portion 521 that includes LED modules 523 in which a plurality of LED units 525 configured of a plurality of LED elements 527 disposed on the PCB and having the same quantity of light are arranged in a longitudinal direction.

Further, the light quantity controller 130 may be configured so that the plurality of LED units 525 generate different quantities of light by the electronic control of the controller 300 to form the light gradient in the LED module 523 in the longitudinal direction.

That is, the light source 520 is provided as the LED substrate portion 521 including the LED element 527, in which the LED substrate portion 521 may include the PCB and the LED module 523. At this time, the LED module 523 may include the horizontally elongated LED units 525 that are arranged in the longitudinal direction, in which the LED unit 525 may include a plurality of longitudinally arranged LED elements 527. The number of LED elements 527 may correspond to the number of wells 111 mounted on the plate 110.

Further, the controller 300 can control the plurality of LED units 525 arranged in the longitudinal direction to have different quantities of light, more preferably, gradually increase the quantity of light from one side in the longitudinal direction toward the other side. Accordingly, the LED module 523 can form the gradient of the quantity of light in the longitudinal direction to longitudinally irradiate various sizes of light to the well 111 mounted on the plate 110.

Since the light quantity controller 130 controls the quantity of light by the electronic control of the MCU provided as the controller 300, it is possible to more precisely and easily provide the user desired quantity of light.

Meanwhile, the LEC substrate portion 521 may be detachably provided on the chamber 101 to be replaced with various kinds of light sources 520.

In detail, like the embodiments illustrated in FIGS. 12 and 13, the LED substrate portion 521 may be bolted to the inside of the cover 103 of the chamber 101 by means of a fastening member 540. When the LED substrate portion 521 is replaced with other types of light sources 520 (for example, an LED module 523 that irradiates different colors), the bolt of the fastening member 540 is separated and thus the LED substrate portion 521 can be replaced with other LED substrate portions 521 to be assembled.

At this time, referring to FIGS. 13 and 14, one side of the LED substrate portion 521 may be provided with a power connection terminal 545 that receives power and quantity of light information from the controller 300. Here, the power connection terminal 545 is provided with a plurality of pins corresponding to pins of the PCB circuit of the LED substrate portion 521 and may be detachably connected to a plurality of electric wires through which signals from the controller 300 are transmitted. Accordingly, even when the LED board 521 is replaced with another LED substrate portion 521, the same quantity of light information can be received from the controller 300 by the power connection terminal 545.

Therefore, even after the LED substrate portion 521 is replaced, the quantity of light is controlled by the light quantity controller 130, such that the culture efficiency can be further improved by being replaced with a type of LED light suitable for cultured photobiology without limitation.

However, the method of installing the LED substrate portion 521 in the chamber is not limited to the illustrated embodiment and may be variously modified as long as the LED substrate portion 521 can be detachably assembled.

On the other hand, the controller 300 may include a constant current IC for allowing a constant current to flow by an external control to supply a constant current to the LED module 523.

That is, the MCU provided as the controller 300 includes the constant current IC, such that a constant magnitude of constant current can be stably supplied to the plurality of LED elements 527 under the control from the outside.

Meanwhile, the high throughput photobioreactor 100 according to the exemplary embodiment of the present invention may include a temperature holding portion that holds a temperature of the well.

The temperature holding portion may prevent radiant heat generated from the light source 120 from arriving at the plate 110 or remove convective heat in the chamber 101 to minimize an influence on the temperature of the well 111 mounted on the plate 110 due to the light source 120. The temperature holding portion may be embodied in the light quantity control film 131 and the gas supplier.

Specifically, the light quantity control film 131 is mounted between the plate 110 and the light source 120 to suppress the radiant heat that is generated from the light source 120 such as an LED element from arriving at the plate 110. Here, as long as the light amount control film 131 can reduce the radiant heat generated from the light source 120, the embodiment of the light amount control film 131 may be various. For example, the light quantity control film 131 may be an optical filter, a membrane for blocking the radiant heat, or the like. Regardless of the light quantity control, a film may be used to reduce the transmission of the radiant heat only.

In addition, the gas supplier may supply fluids such as carbon dioxide and air to the chamber 101 to generate an air circulation inside the chamber 101, thereby removing the convective heat due to the light source 120. Accordingly, the transfer of the heat generated from the light source 120 to the plate 110 due to the convection may be minimized.

According to the embodiment of the present invention, the temperature holding portion may solve the problem that the temperature of the plate 110 is changed due to the radiant heat and the convective heat when the light is irradiated by the conventional light source 120, such that the temperature of the plate 110 can be precisely controlled by the temperature provided by the temperature controller 600. In particular, when a TEC module is applied as an example of the temperature controller 600 according to the embodiment of the present invention, the temperature of the low temperature area can be set, such that the temperature of the low temperature area can also be held by the temperature holding portion.

However, the temperature holding portion is not limited to the above-described embodiment, but various modifications can be made as long as it can minimize the radiation heat or the convection heat radiated from the light source to the plate.

Meanwhile, referring to the embodiments described with reference to FIGS. 15 and 16, the high throughput photobioreactor 100 according to another embodiment of the present invention is installed to surround the edge of the plate 110, and may further include a well holder 115 for allowing the plate 110 to adhere to the temperature gradient block 630 by an own weight.

That is, the well holder 115 has a shape corresponding to the shape of the plate 110, and may be formed in a frame form having a hollow portion into which the edge of the plate 110 can be fitted. More preferably, the well holder 115 may be made of a metal having a large mass.

Accordingly, the plate 110 can further adhere to the temperature gradient block 630 by the own weight of the well holder 115. Therefore, the well holder 115 can provide the effect of efficiently transferring the temperature of the temperature gradient block 630 to the plate 110 by allowing the plate 110 to adhere to the temperature gradient block 630.

Meanwhile, referring to FIGS. 15 and 16, the photobioreactor 100 according to another embodiment of the present invention may further include the vibrator 700 that is coupled to the well holder 115 and generates vibrations of the plate 110 to perform an agitation operation in the well 111.

That is, since the edge of the plate 110 is fitted into the well holder 115, if the vibrator 700 vibrates the well holder 115, the photobiology contained in the well 111 can be agitated while vibrations are transmitted to the whole of the plate 110. At this time, the vibrator 700 may be, for example, a vibration motor, but is not limited thereto, and can be variously modified as long as it can vibrate the plate 110.

More preferably, a plurality of vibrating means 700 may be provided in the well holder 115 while being spaced apart from each other. That is, the illustrated embodiment describes the case in which two well holders 115 are provided vertically but the number of well holders is not limited thereto, and therefore three or more vibration motors may be disposed at regular intervals.

Accordingly, it is possible to provide an effect of evenly transmitting vibrations to the whole of the plate 110.

According to the high throughput photobioreactor according to the embodiment of the present invention, it is possible to establish the optimal production conditions by constructing various wide ranges of temperature conditions to cultivate the microorganisms in various environments.

If the high throughput photobioreactor according to another embodiment of the present invention is used, the controller for electronically controlling the temperature and the quantity of light and the monitor connected to the controller can be more precisely set the optimal conditions necessary for the production of microalgae and even by the unskilled researchers can easily and conveniently control the quantity of light, the temperature, or the like.

Although the present invention has been shown and described with reference to specific embodiments thereof, it will be readily understood by those skilled in the art that the present invention can be variously modified and changed without departing from the spirit and scope of the invention as set forth in the following claims.

The invention claimed is:

1. A high throughput photobioreactor, comprising:
   a chamber;
   a plate installed in the chamber and mounted with a plurality of wells;
   a plurality of light sources installed in the chamber and irradiating light toward the plate;
   a light quantity controller positioned on an upper part of the plate to make quantities of light irradiated to the plurality of wells different; and
   a temperature controller controlling a temperature of the plate;
   a well holder formed in a frame form having a hollow portion into which the plate is fitted;
   a plurality of vibrators coupled to the well holder to be spaced apart from each other and vibrating the plate to perform an agitation operation in the wells; and
   wherein the temperature controller includes a plate-like temperature gradient block installed so that an upper surface thereof comes into surface contact with a lower surface of the plate and having a temperature gradient formed by heating or cooling both ends thereof at different temperatures;

the well holder makes the plate pressed to the temperature gradient block by the well holder's own weight; and wherein the plate includes a mounting groove formed concavely in the lower surface thereof, and the temperature gradient block includes a mounting protrusion protruded corresponding to the mounting groove and inserted into the mounting groove.

2. The high throughput photobioreactor of claim 1, wherein the plurality of light sources are provided as either light emitting diodes (LEDs) or organic light emitting diodes (OLEDs).

3. The high throughput photobioreactor of claim 1, wherein the light quantity controller is a light quantity control film that is disposed between the plate and the plurality of light sources and has a gradation.

4. The high throughput photobioreactor of claim 3, wherein the light quantity control film is formed to have a gradation at which a color is getting more transparent from an achromatic color from one side toward the other side in a longitudinal direction.

5. The high throughput photobioreactor of claim 3, wherein the light quantity control film is formed to have a gradation at which a color is getting more transparent from a chromatic color from one side toward the other side in a longitudinal direction.

6. The high throughput photobioreactor of claim 1, wherein the light quantity controller is a dimmer connected to the plurality of light sources to control a supply amount of current to control brightness of the light source.

7. The high throughput photobioreactor of claim 6, wherein the plurality of light sources are formed in at least two groups which are longitudinally disposed to be spaced from each other, and at least two dimmers are provided to be connected to the light sources of the groups to control the quantities of light to be different according to each group.

8. The high throughput photobioreactor of claim 1, wherein the temperature controller includes:

a temperature control block including a first temperature control pipe positioned at a lower part of the plate and injected with hot water or heated air to control a temperature of the plate and a second temperature control pipe injected with cooling water or cooling air to control a temperature of the plate; and a temperature diffusion plate positioned between the temperature control block and the plate to keep the temperature of the plate.

9. The high throughput photobioreactor of claim 8, wherein the first temperature control pipe and the second temperature control pipe are disposed to be spaced apart from each other in a lateral direction.

10. The high throughput photobioreactor of claim 1, wherein the temperature controller includes:

a plurality of semiconductor elements extending in a longitudinal direction of the plate; and a temperature control device heating or cooling at least one of the plurality of semiconductor elements to control the temperature of the plate, and the plurality of semiconductor elements are disposed to be spaced apart from each other in a lateral direction.

11. The high throughput photobioreactor of claim 1, further comprising:

a controller controlling the quantity of light of the light quantity controller and the temperature of the temperature controller; and a monitor receiving a signal about the temperature and the quantity of light from the controller and visually displaying the signal and receiving setting of a user for the control of the controller.

12. The high throughput photobioreactor of claim 11, wherein the temperature controller includes:

a first thermo electric cooling (TEC) module heated or cooled at a temperature input by the controller;

a second TEC module installed to be spaced apart from the first TEC module and receive a temperature higher than that of the first TEC module by the controller and the temperature gradient block is installed so that a lower surface of one side thereof comes into contact with the first TEC module and a lower surface of the other side thereof comes into contact with the second TEC module to allow the first TEC module and the second TEC module to heat or cool both ends thereof at different temperatures, thereby forming a temperature gradient, and the temperature of the plate is controlled while the temperature gradient is generated in the plurality of wells in a lateral direction by a temperature difference between the first TEC module and the second TEC module.

13. The high throughput photobioreactor of claim 12, wherein the temperature controller further includes a temperature sensor attached to the first TEC module and the second TEC module to detect the temperature.

14. The high throughput photobioreactor of claim 12, wherein the controller finely raises or lowers the temperature of the first TEC module and the second TEC module by a pulse width modulation (PWM) control.

15. The high throughput photobioreactor of claim 11, wherein the plurality of light sources are configured to include a printed circuit board (PCB) on which a predetermined circuit pattern is formed and an LED substrate portion that includes an LED module in which a plurality of LED units configured of a plurality of LED elements disposed on the PCB and having the same quantity of light are arranged in a longitudinal direction, and the light quantity controller is configured so that the plurality of LED units generate different quantities of light by an electronic control of the controller to form a light gradient in the LED module in a longitudinal direction.

16. The high throughput photobioreactor of claim 15, wherein the LED substrate portion is detachably to the chamber to be replaced with various kinds of light sources.

17. The high throughput photobioreactor of claim 15, wherein the controller includes a constant current IC that allows a constant current to flow by an external control to supply a constant current to an LED module.

18. The high throughput photobioreactor of claim 1, further comprising:

a gas supplier supplying carbon dioxide into the chamber.

19. The high throughput photobioreactor of claim 18, wherein the gas supplier includes:

a supply pipe connected to the chamber; and a supply pump installed on one side of the supply pipe and configured to perform pumping to supply the carbon dioxide into the chamber.

* * * * *